United States Patent
Cole et al.

[11] Patent Number: 6,142,023
[45] Date of Patent: *Nov. 7, 2000

[54] METHOD AND APPARATUS FOR APPLYING A PREDETERMINED PROOF LOAD TO A CABLE AND MEASURING THE RESULTANT CABLE LENGTH

[75] Inventors: Michael C. Cole, Spanaway; David M. Kozy, Kent, both of Wash.

[73] Assignee: The Boeing Company, Seattle, Wash.

[*] Notice: Under 35 U.S.C. 154(b), the term of this patent shall be extended for 449 days.

[21] Appl. No.: 08/559,117

[22] Filed: Nov. 17, 1995

[51] Int. Cl.$^7$ .................................................. G01N 3/08
[52] U.S. Cl. ............................................. 73/828; 73/862.41
[58] Field of Search .............................. 73/789, 828, 785, 73/158, 826, 862.41

[56] References Cited

U.S. PATENT DOCUMENTS

| | | | |
|---|---|---|---|
| 2,421,002 | 5/1947 | Babcock | 73/828 |
| 2,875,609 | 3/1959 | Seney | 73/826 |
| 3,010,311 | 11/1961 | Meldrum et al. | 73/828 |
| 3,379,054 | 4/1968 | Folweiler | 73/828 |
| 3,486,372 | 12/1969 | Lange | 73/828 |
| 3,969,930 | 7/1976 | Prevorsek et al. | 73/785 |
| 4,302,979 | 12/1981 | Dykmans | 73/828 |
| 4,338,565 | 7/1982 | Hall | 324/206 |
| 4,372,154 | 2/1983 | Corbin | 73/104 |
| 4,562,743 | 1/1986 | Bonine | 73/828 |
| 4,718,168 | 1/1988 | Kerr | 73/158 |
| 4,756,188 | 7/1988 | Fennell | 73/158 |
| 5,265,476 | 11/1993 | Khachaturian et al. | 73/828 |

FOREIGN PATENT DOCUMENTS

| | | | |
|---|---|---|---|
| 148101 | 5/1981 | Germany . | |
| 232985 | 2/1986 | Germany | 364/562 |

*Primary Examiner*—Max Noori
*Attorney, Agent, or Firm*—James P. Hamley

[57] ABSTRACT

A system for applying a predetermined proof load to a control cable and measuring the resultant cable length thereof includes a motor (32) which, under the control of a controller (14) drives an actuator (28) which, in turn, controllably displaces an end fixture (26). The exact distance moved by the end fixture (26) is monitored by an encoder (34) and a load cell (27) monitors actual loading on a cable under test. A home position sensor (30) provides input to the controller (14) to indicate whether or not the end fixture (26) is homed to its reference position. During cable testing, the fixed end of the cable is fixedly attached to a predetermined position in a channel (20). The free end of the cable is then attached to the end fixture (26). The controller (14) actuates the motor (32) to thereby provide a predetermined proof load profile to the cable under test. At the end of the proof loading test, the controller (14) determines, via the encoder (34), the distance $L_2$ that the end fixture, and thus the cable have moved from the home position. This distance $L_2$ is added to the initial distance $L_1$ from the home position to the fixed anchor hole (23) to thereby determine an overall length L of the cable.

14 Claims, 7 Drawing Sheets

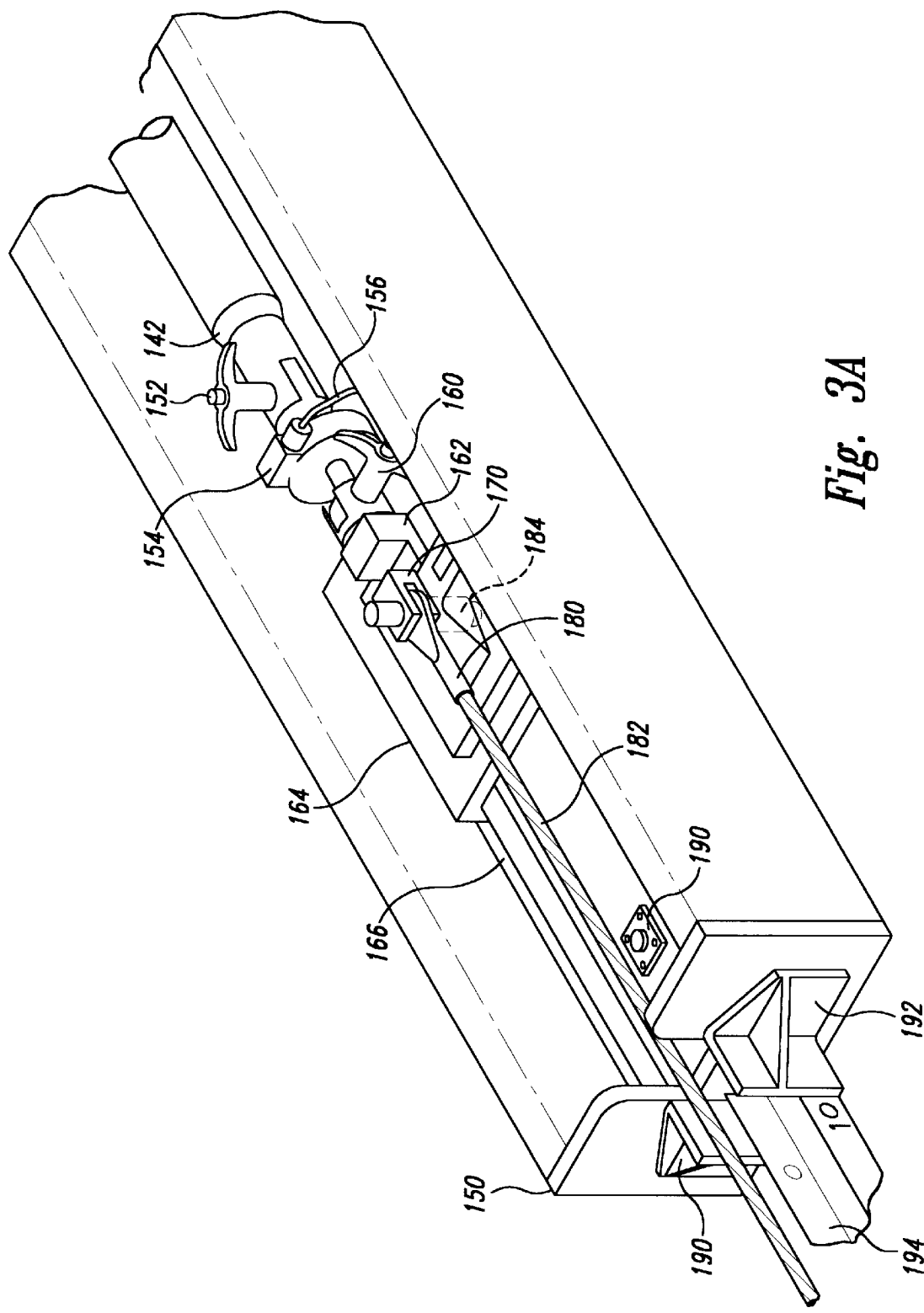

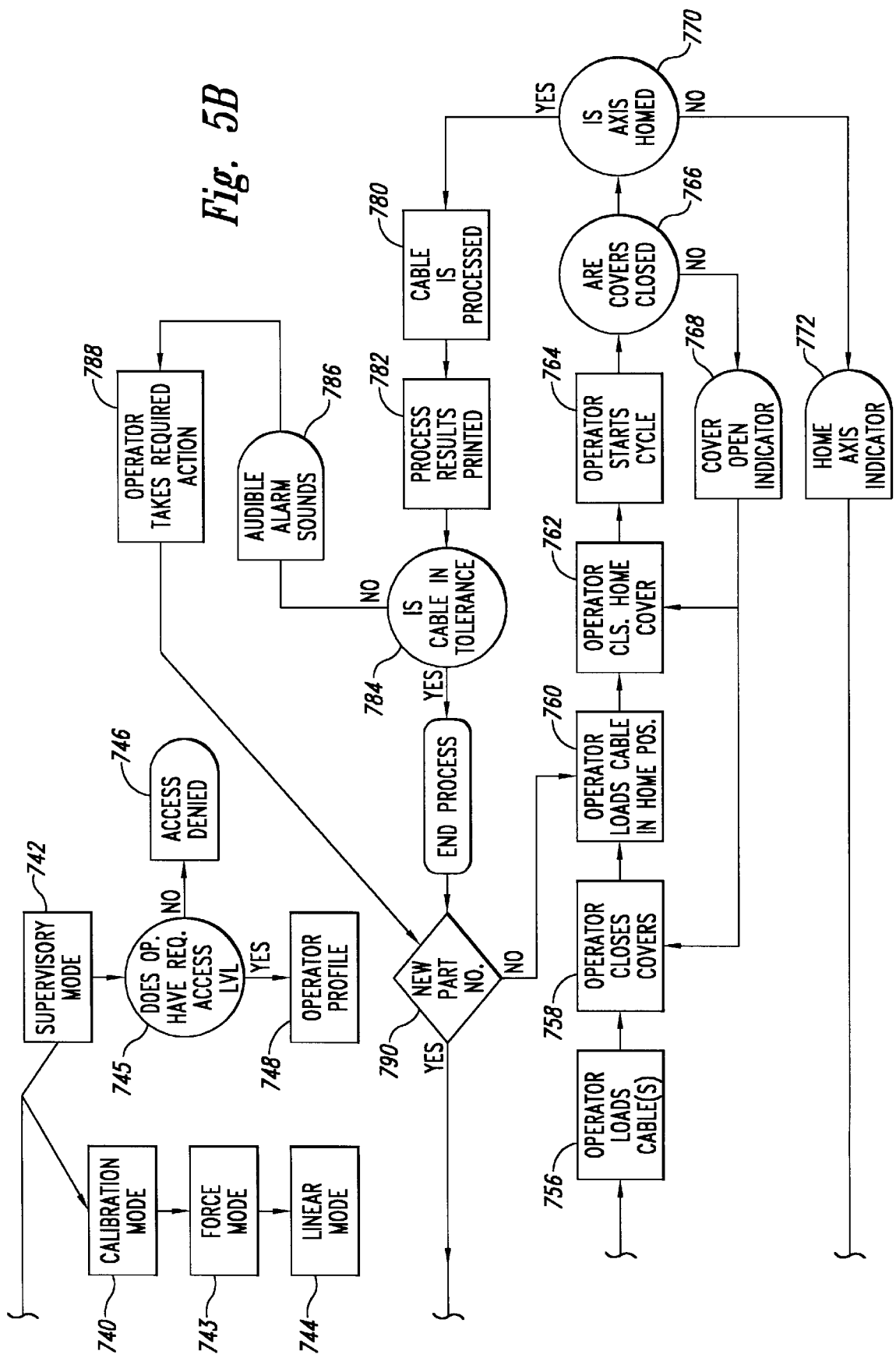

METHOD AND APPARATUS FOR APPLYING A PREDETERMINED PROOF LOAD TO A CABLE AND MEASURING THE RESULTANT CABLE LENGTH

BACKGROUND OF THE INVENTION

The present invention relates to the control cable art and, in particular, to a method and apparatus for applying a predetermined proof loading to a cable and measuring the resultant cable length.

Numerous applications exist in which a control cable is used to control the position of moveable structure. One such application is in the aircraft art wherein aircraft wire cable assemblies are used to actuate control surfaces such as rudders and flaps. These cables must be proof loaded (pre-stretched) and the length measured before installation in the aircraft. The process for proof loading must comply with detailed specifications. For example, the specifications will detail the rate at which a specific proof load should be applied and the duration at maximum loading.

Prior to the present invention, the common method for proof loading a cable has been to apply a tension load to the cable with a hydraulic cylinder or electric power lead screw. An operator monitors the rate at which proof loading is applied and the total duration of the maximum proof load with a wrist watch. The tension force is measured with an analog force gauge and the overall length of the cable is measured at a separate location with a measuring tape.

This present method of proof loading and length measuring is time consuming, tedious and subject to human error. Also, the present method does not afford the means for collecting cable history data other than via human observation.

There is a long felt need in this art, therefore, for a reliable method and apparatus for applying a predetermined proof load to a cable and measuring the resultant cable length.

SUMMARY OF THE INVENTION

It is an object of the present invention, therefore, to provide an improved method and apparatus for applying a predetermined proof loading to a cable and measuring the resultant cable length.

Other objects of the invention will become understood in greater detail upon review of the specification and claims set forth herein below.

In summary, the inventive apparatus for applying a predetermined proof load to a cable under test and measuring the resultant cable length comprises a means for fixing one end of the cable at a predetermined position. Suitable means are provided for attaching the free end of the cable to an actuator controlled fixture. A means for positioning the actuator at a home position, which home position is a predetermined distance, $L_1$, from said fixed position are provided. A load sensor senses the loading on the cable. A controller:

a) controllably actuates the actuator to apply a predetermined load to the cable,
b) determines the distance, $L_2$, of the actuator controlled fixture from said home position, and
c) sums the distance of $L_1$ and $L_2$ to thereby calculate the resultant cable length L.

In a further aspect of the invention, the above apparatus includes a means for identifying the particular cable under test. Provided memory stores the resultant cable length tolerances for the particular cable under test and a comparator compares the actual resultant cable length L with the stored cable length tolerances to produce an indication of the cable under test being within or outside of the specified tolerances.

In yet a further aspect of the invention, the provided means for identifying the particular cable under test includes a keypad means for permitting an operator of the apparatus to manually key in the part number of the cable under test.

In yet a further aspect of the invention, the cable under test includes a bar-code indicating the part number for the cable and the provided means for identifying the cable under test includes a bar-code reader for reading the cable provided bar-code.

In yet a further aspect of the invention, the inventive controller includes means responsive to identifying the particular cable under test to indicate to the apparatus operator the specific end position to which the cable under test should be affixed to thereby perform the proof loading test on the particular cable under test.

The inventive method for applying a predetermined proof load to a cable under test and measuring the resultant cable length comprises the steps of:

a) fixing one end of the cable at a predetermined position,
b) attaching the free end of the cable to an actuator controlled fixture,
c) positioning the actuator controlled fixture at a home position, which home position is a predetermined distance $L_1$ from the fixed position,
d) sensing the loading on the cable,
e) controllably actuating the actuator to apply a predetermined loading to the cable,
f) determining the distance $L_2$ of the actuator controlled fixture from the home position, and
g) summing the distances $L_1$ and $L_2$ to calculate the resultant cable length L.

In yet a further aspect of the above method, additional steps include:

identifying the particular cable under test,
storing the resultant cable length tolerances for the particular cable under test, and
comparing the actual cable length L with the stored resultant cable tolerances and producing an indication of whether the cable under test is within or without the tolerances.

In yet a further aspect of the above-described method, the step of identifying the particular cable under test includes the further step of providing keypad means for permitting an operator to manually key in the part number of the cable under test.

In yet a further aspect of the inventive method, additional steps include:

bar-coding the cable under test to indicate the part number thereof, and providing a bar-code reader for reading the bar-code.

In yet a further aspect of the above inventive method, an additional step includes indicating to the operator the specific fixed end position to which the cable under test should be affixed to thereby perform the proof loading test on the cable under test.

BRIEF DESCRIPTION OF THE DRAWINGS

FIG. 3A is a perspective, exploded view of the home position fixture;

FIGS. 5A and 5B are logic flow diagrams illustrating the sequence of steps performed by the preferred embodiment of the invention.

DETAILED DESCRIPTION

Figure 1:
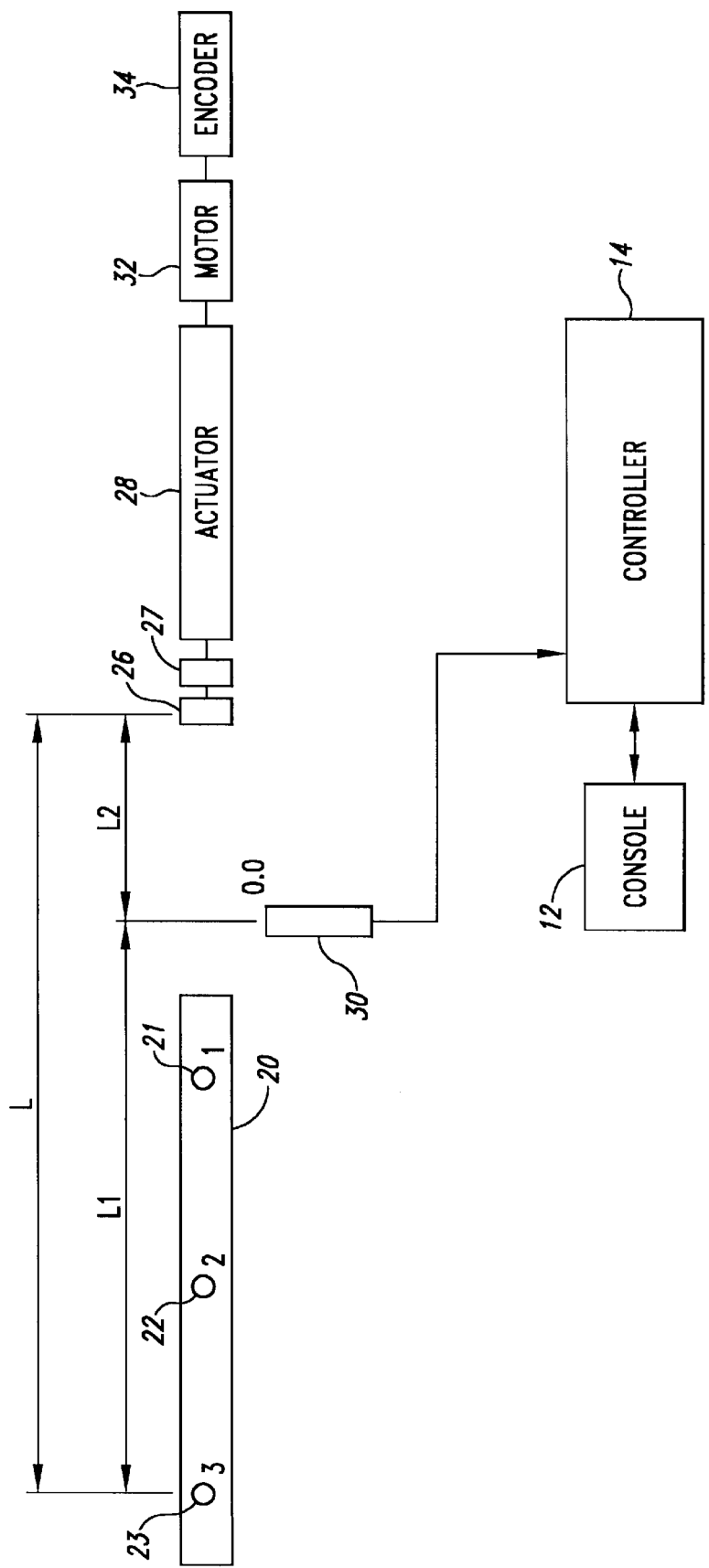
FIG. 1 is a block diagram illustrating the primary components of the proof loading apparatus and also indicates the geometric relationships which define the resultant cable length.

FIG. 1 is a block diagram illustrating the principle components of the preferred embodiment of the invention and schematically depicts the manner by which a defined proof load is applied to a cable under test and the resultant cable length is measured.

Operator interface to the system is provided via a console 12. The console is provided with a display to allow operator input and review of information, a keypad to provide operator input and, in the preferred embodiment of the invention, a bar-code scanner which allows an operator to scan a bar-code provided with a cable to thereby identify cable parameters.

The console 12 is connected to an electronic controller 14. Electronic controller 14 includes a central processing unit and associated memory which is used to perform the detailed operations as set forth herein below. The controller 14 also stores information relating to each particular cable under test. This information can be compared by the controller with actual measurements taken on a cable under test, to thereby determine whether or not the cable meets defined tolerances.

The cable under test is attached at one end to a fixed position on a channel 20. The channel 20 contains a plurality of numbered hole positions 21–23, for example, each of which has an associated number. Once the part number of the cable has been identified, an operator affixes an end of the cable to one of the specified, predeterminedly positioned holes 21–23. This fixed position can be determined by the controller via it's internal memory and displayed to the operator via the console 12.

With one end of the cable at a fixed position 21–23, the free end of the cable is then attached to a home position fixture 26 which is under the control of an actuator 28. At initial setup, the actuator 28 literally moves the home position fixture 26 to a home position, as sensed by a home position sensor 30. The home position sensor 30 constitutes an input to the controller 14. The home position is a predetermined distance from the channel fixed positions 21–23. Thus, for a given cable under test, the nominal length of the pretested cable is a given distance $L_1$ from the home position to the defined channel position.

A load cell 27 is interposed between the home position fixture 26 and the actuator 28. The function of the load cell 27 is to provide an input to the controller 14 of the actual loading on the cable under test.

Power to the actuator 28 is provided by a motor 32 which is under control of the controller 14. The angular rotation of the motor 32 and, thus via actuator 28, the linear position of the home position fixture 26 is monitored by an encoder 34. The output from the encoder 34 is an input to the controller 14.

In operation, the operator first homes the home position fixture to the home position as determined by the home sensor 30 input to the controller 14. Then, a particular cable to be tested is identified and it's nominal length determined. If this is done via a bar-code scan of the bar-code associated with the cable under test, the controller, via it's internal memory "looks up" the cable to be tested and displays to the operator, via the display in the console 12, the proper position 21–23 for the fixed end of the cable. The operator then proceeds to affix one end of the cable to the appropriate channel position 21–23.

As determined either manually via the console 12 by operator input, or under its own internal automatic control, the controller then proceeds to apply a predetermined proof load at a predetermined rate to the cable under test.

Figure 2:
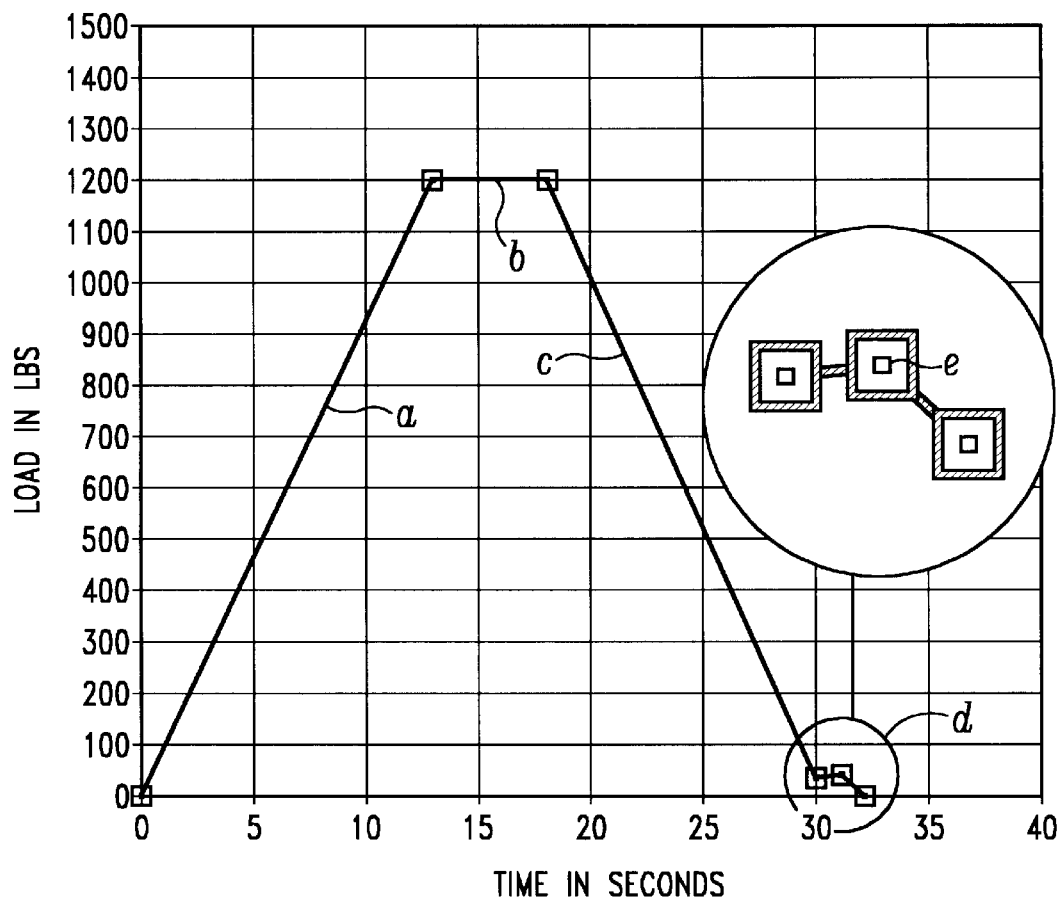
FIG. 2 is a graph indicating a typical rate of applied proof loading to a cable under test, the dwell time at full load and the resultant measurement of cable length.

An actual proof loading test is depicted graphically in FIG. 2. Shown is a graph of load in pounds applied to a cable under test versus time in seconds. In this controlled test, the controller 14 via the motor 32, actuator 28, load cell 27 and home position fixture 26 ramp up a load on the cable under test at a predefined rate, as depicted by graph portion (a). Once the controller determines that the predetermined maximum load has been applied to the cable, this load is held for predetermined dwell time, as represented by graph portion (b). Following the dwell proof load, the controller then activates motor 32 to reduce the loading on the cable at a predetermined rate as determined by graph portion (c).

In graph portion (d) of FIG. 2, the loading on the cable has been reduced below a predetermined test load, and then increased back to a fixed load test point as represented by portion (e). It is this test point (e) that (referring to FIG. 1) the controller uses to determine the distance from the initial home position to the new post-test stretch length of the cable, such distance being designated $L_2$. Finally, the controller reduces the loading on the cable to zero, as shown in FIG. 2, and calculates the overall proof load length of the cable as $L=L_1+L_2$ The controller 14 may then compare via its internal memory and CPU, the stretch length of the cable to defined tolerances for cables of that model type. Whether the cable under test is within or without the defined tolerances can then be displayed to the operator via the display in console 12.

In addition, having stored data concerning previous cable testing, the controller 14 can calculate and display or print statistical data relating to long term cable test results.

Figure 3:
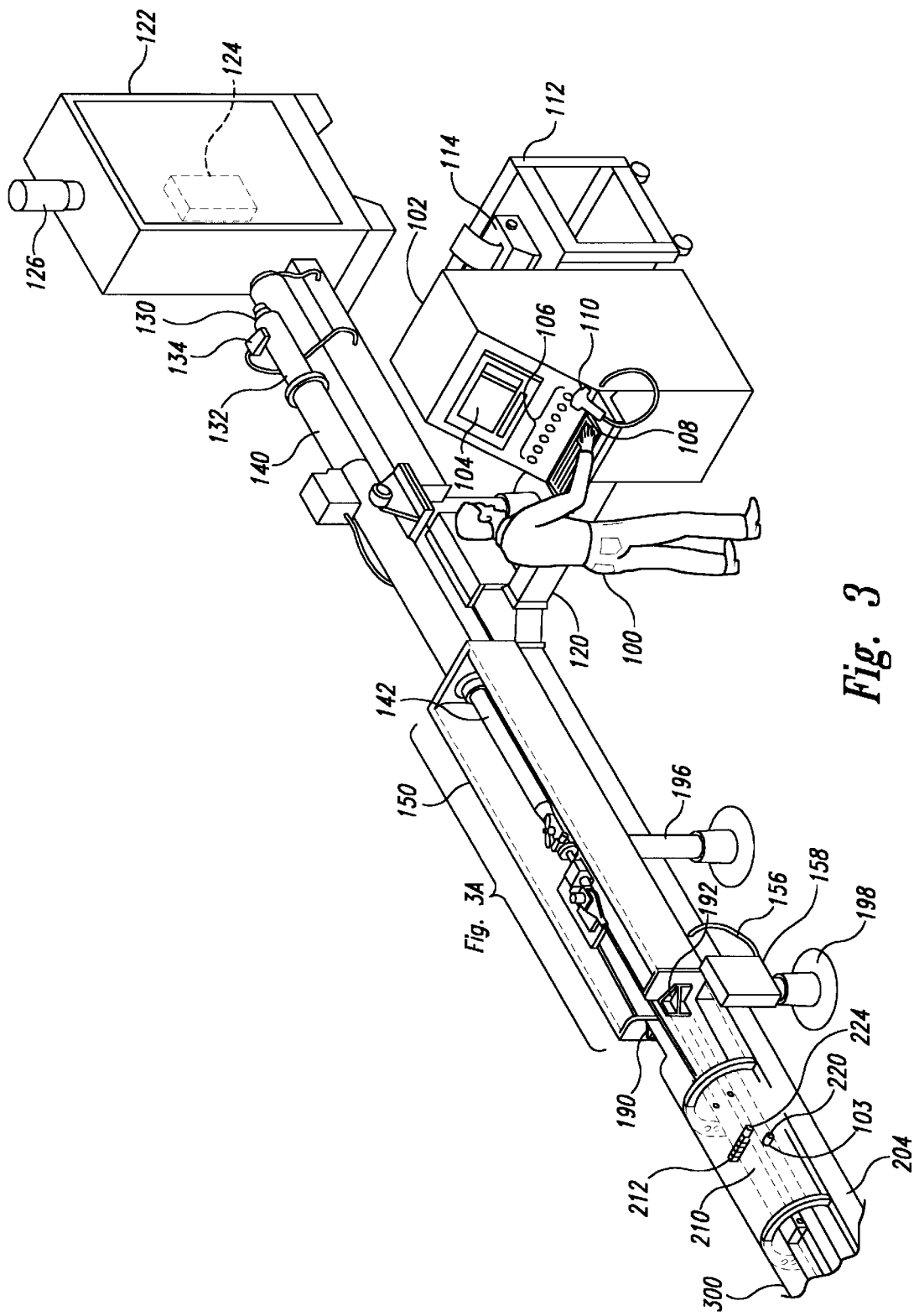
FIG. 3 is a perspective, detailed diagram illustrating the overall construction of the preferred embodiment of the invention.

FIG. 3 is a detailed, perspective diagram of the components used in the preferred embodiment of the invention. Shown is an operator 100 standing at the system console 102. The system console 102 is provided with a display screen 104, a series of user controlled mechanical switches 106, a user input keypad 108 and a bar-code scanner 110. Associated with the console 102 is a cart 112 which carries a printer 114. The printer connects to the console 102 and, under operator, control can print out data relating to the cable under test.

Electrical connections from the console 102 are routed through a wire way 120 to a main electrical cabinet 122. Provided in the main electrical cabinet 122 is the electronic control system circuitry, indicated generally at 124. Atop the main electrical cabinet 122 is a status beacon 126 which indicates to those in the vicinity of the test apparatus the current status of the system.

Connections from the electronic control system circuitry 124 are routed through the main electrical cabinet 122 and through the wire way 120.

A connection is made to an encoder 130. Encoder 130 attaches to a servo motor 132 which, in turn, connects via a connection box 134 through the wire way 120 into the electronic control system circuitry 124.

The servo motor 132 connects to an actuator 140 including a gear reducer which, in turn, drives an actuator shaft 142. An actuator forward and reverse limit switch assembly 144 senses for the maximum forward or reverse position allowed by the actuator and, should the actuator position exceed such maximum limits, the appropriate forward or reverse limit switch is actuated which, via a wire way connection to the electronic control system 124, causes the system to cease further actuation.

FIG. 3A is an exploded view of the home position fixture 150. The actuator shaft 142 connects via an actuator coupling pin 152 to a load cell assembly 154. The load cell assembly, in the normal manner, senses the loading which is ultimately applied to the cable and provides a corresponding electrical signal output over a line 156 to a load cell and home position junction box 158. Included within the load cell and home sensor junction box 158 is a load cell amplifier for amplifying the load cell produced signal and routing it via the wire way 120 to the electronic control system electronics 124.

The load cell 154 connects through a load cell coupling pin 160 to a yoke assembly 162.

The yoke assembly 162 is fixedly connected to a carriage assembly 164. The carriage, in turn, includes brackets to ride on a set of rails, one of which is depicted at 166. Thus, under control of the actuator shaft 142, the entire carriage assembly may be driven up or down the rails.

Attached to the yoke assembly 162 is an end fitting fixture 170. End fitting fixture 170 is appropriately constructed to receive and secure end fitting 180 of the cable under test 182. In addition, an extended portion 184 of the home position fixture 170 is designed to be electrically sensed by a home position sensor 190 when the home position fixture 170 is positioned directly opposite the home position sensor 190. The home position sensor 190 provides an electrical output signal which is routed through the wire way 120 to the electronic control system circuitry 124.

The home position fixture 150 is mechanically attached via channel attachment brackets 190, 192 to the cable channel 194. The home position fixture 150, and the cable channel 194, are supported above ground position by provided stands, such as stands 196 and 198.

The cable channel 194 includes a series of predeterminedly located and numbered hole positions, such as hole positions 201–204, which are transversely drilled through the cable channel 194. Designed to ride within the cable channel 194 is a slide block 210. Fixedly mounted in position on the slide block 210 is anchor tooling 212. Provided in slide block 210 is a mounting hole which, via a suitable anchor pin 220, allows the slide block 210 to be fixedly positioned within a given one of the channel hole positions 201–204. In addition, the anchor tooling 212 is provided with a retaining pin 224 which is used to secure one end of a cable under test 182 to the anchor tooling 212.

A protective Lexan cover 300 may be rotated into position over the cable under test 182.

In operation, a part number for a given cable to be tested is identified. This can either be done by input of the operator 100 via the keypad 108 or, if the cable is provided with bar-coding, the operator 100 can use the bar-code scanner 110 to scan the appropriate bar-code.

The part number of the cable to be tested is then sent to the electronic control system circuitry 124, wherein data is recalled from memory relating to the test procedure for that particular cable. Electronic control system circuitry 124 relays to the console display 104 a message indicating to the operator the particular one of the anchor pin holes 201–204 that the slide block 210 should be aligned with. The operator 100 then moves the slide block into position and secures it with the anchor pin 220. The end of the cable is then attached to the appropriate anchor tooling 212 and secured in place by the anchor tooling pin 224.

Also, the electronic control system circuitry 124 actuates the motor 132 to drive the actuator 140 and the actuator shaft 142 such that the home tooling fixture end fitting 170 is directly aligned opposite the home position sensor 190. Now, upon appropriate input from the operator 100 via input switches 106, a Lexan cover 300 is closed to protect the operator from cable debris in the event of a cable failure.

Then, the electronic control system circuitry 124, at a predefined rate as determined by the specification stored in memory for the cable under test, drives the motor 132 to thereby actuate the actuator 140 and begin a stretching of the cable 182 under test. Feedback of actual cable load is provided to the electronic control system circuitry 124 via the load cell 154. Once the cable has been subjected to the predetermined maximum load, the electronic control system electronics 124 then holds the applied load for a predetermined dwell time, followed by a relaxing of the stress on the cable 182 to a point just below, and then backup to, the test load to measure the resultant length of the cable.

Since the encoder 130 monitors the rotational position of the servo motor 132, electronic data is provided to the electronic control system circuitry 124 as to the total movement $L_2$ of the home fixture tooling 170 from the home position. The initial length of the cable pretest was known to the system via the fact that the initial home fixture tooling 170 was opposite the home position sensor 190 and that the distal end of the cable 182 was fixed in a predetermined position from the home position. As such, the electronic control system 124 can calculate a total post proof load length L of the cable by simply adding the initial length $L_1$ to the added length $L_2$. By comparing the total length L for cable under test with the tolerances stored in memory for that particular model, the electronic control system electronics 124 can indicate to the operator 100 via the display 104 whether the tested cable is within or outside of the specified tolerances.

Figure 4:
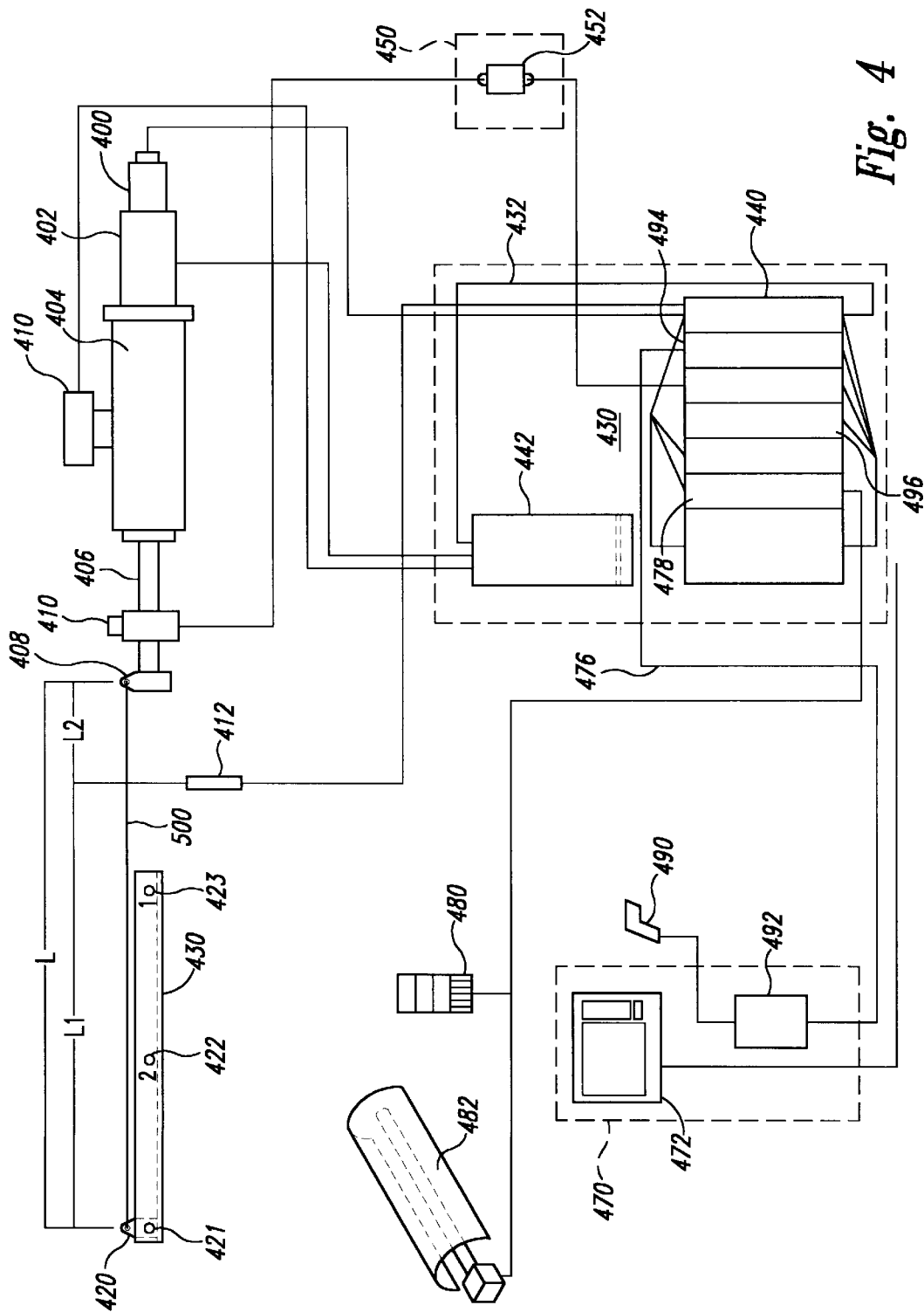
FIG. 4 is a schematic diagram illustrating the interconnection of the various principle components to the preferred embodiment of the invention.

FIG. 4 is a schematic diagram illustrating the electrical interconnection among the various components of the preferred embodiment of the system. An encoder 400 mechanically connects to a servo motor 402 which, in turn, connects to an actuator 404. The actuator, via an actuator shaft 406, connects to a home tooling fixture 408. A load cell 410 monitors the loading on the cable under test. Affixed to the actuator 404 are forward and reverse limit switches 410. These switches detect the condition of the actuator 404 having traveled to either its forward or reverse limits. A home position sensor 412 is positioned at the "home" location for the fixture 408. The fixture 408 receives one end of the cable under test, with its remaining end connected to an end fitting 420, which is at a fixed location in a predetermined one of multiple position holes 421–423 in a channel 430.

Control of the system is provided via electronic control circuitry, indicated generally at 430, which is provided in a main electrical cabinet 432. In particular, digital pulses from the encoder 400 which thereby indicate rotational position of servo motor 402 and linear position of actuator 404 are fed to a motion control module 440. Power to drive the servo motor 402 is provided from a servo amplifier module 442. Also fed as an input to the servo amplifier module 442 are the outputs from the forward and reverse limit switches 410. If either of these switches is actuated, meaning that the actuator has moved to its forward or reverse limits, the signal supplied to the servo amplifier 442 causes power disruption to the servo motor 402 whereby the system operation stops.

Servo amplifier 442 receives its control signal from the motion control module 440.

The load cell 410 produces an output signal representative of the loading on the cable under test. This signal is routed to a junction box 450 which contains a load cell amplifier 452. The resulting amplified load cell signal is fed to an analog input module 454. The output from the home position sensor 402 indicates whether or not the fixture 408 is directly opposite the home position is also fed to the motion control module 440.

Operator input to the system is provided via an operator console 470. The console includes an operator interface and screen display module 472. User inputs to the logic control system 430 as well as feedback from the system to the operator screen are provided via a programmable logic controller 476. A DC output module 478 from the electronic control system 430 activates a status beacon 480 which indicates the status of the system and activates the safety covers 482 which cover the cable under test.

A bar-code scanner 490 provided on the operator console 470 is used to scan bar-code data off of the cable to be tested. The bar-code scanner data is fed to a bar-code interface module 492 in the operator console 470 before being passed to a bar-code module 494. A DC input module 496 receives signals from the home sensor and the safety covers 482 to indicate whether or not it is safe for the system to proceed with the test.

As described above, in operation an operator at the console 470, possibly with the aid of the bar-code scanner 490, will input data relating to the particular cable to be tested. The identification of the particular cable is routed to the programmable logic controller 476 which extracts from internal memory specifications of the particular cable under test. The programmable logic controller 476 then relays to the operator interface screen 472 that particular channel position hole 421–423 to which the end fitting 420 should be affixed. One end of the cable under test 500 is then affixed to the end fitting 420.

The programmable logic controller 476 also sends a signal to the motion control module 440 such that the servo motor 402 actuates the actuator 404 to move the home position fixture 408 to the home position, as determined by home position sensor 412. Now, the free end of the cable is affixed to the fixture 408.

In response to the recall of the stored testing profile from the programmable logic controller 476, the motion control module 440 actuates the servo motor to begin the predetermined testing profile for the cable under test. Actual cable loading is sensed by the load cell 410 and the resultant signal is routed through the load cell amplifier 452 to analog input module 454. This actual load cell information is used by the programmable logic controller to assure proper loading of the cable in accordance with the specified loading profile. The actual position of the fixture 408 and, therefore free end of the cable 500 is determined by encoder 400 which monitors angular position of the servo motor 402 and thereby linear position of fixture 408.

In this manner, the system provides a predetermined load profile to the cable, holds a maximum loading for predetermined dwell time, and then reduces the loading on the cable to below a test position raising it again to a test position and thereby measuring the distance $L_2$ which the end fixture 408 moved from the initial home position. This distance may be added by the programmable logic controller 476 to the initial distance $L_1$ measured from the home position to the predetermined tooling anchor hole 421–423 to thereby calculate the total length L of the cable after proof loading. The programmable logic controller 476 then compares the total length L of the cable to stored tolerance values, thereby indicating to the operator via the console interface screen 472 whether or not the resulting cable length is within defined tolerances.

Figure 5A:
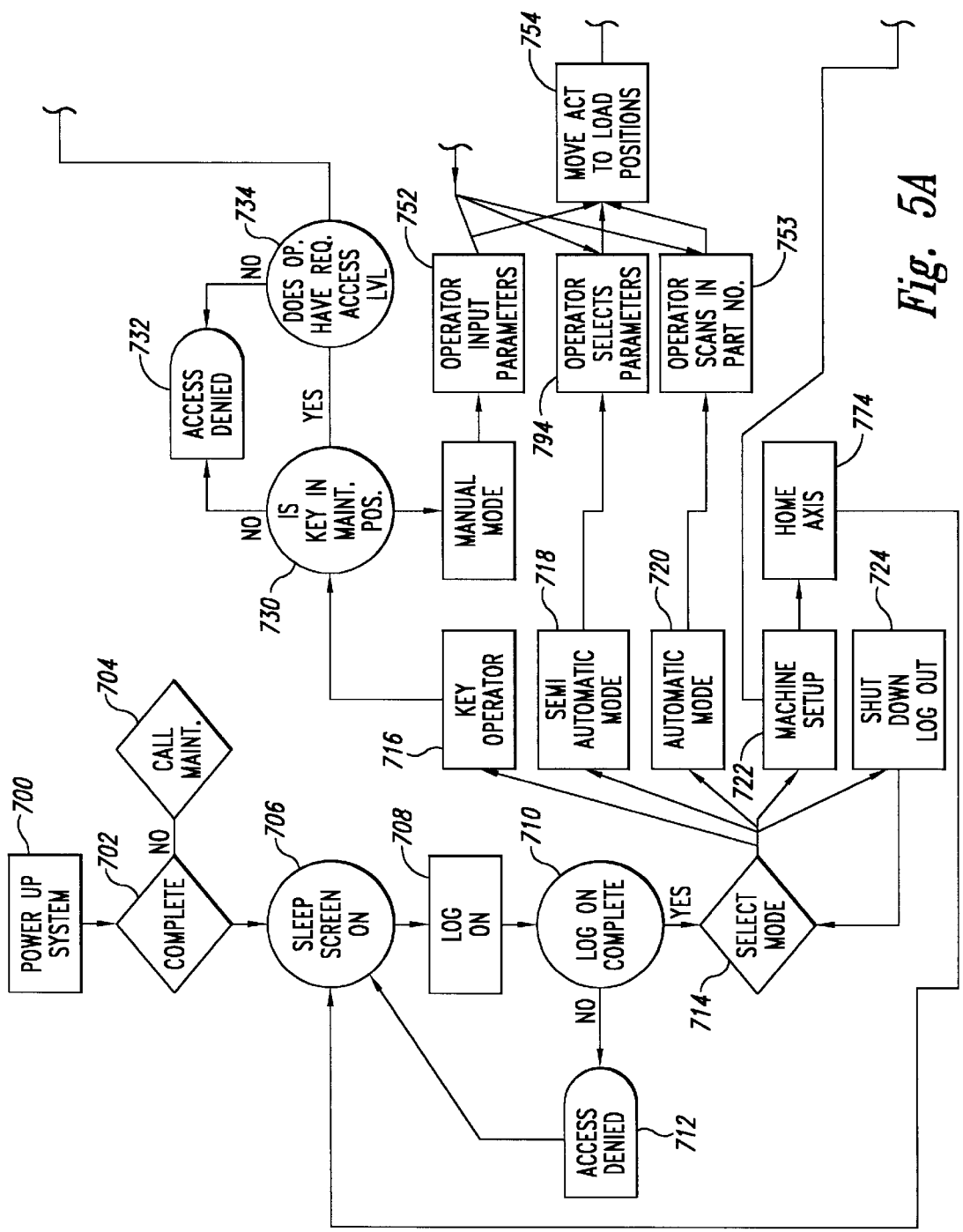

FIGS. 5A and 5B are logic flow diagrams illustrating the sequential logic steps performed by the system in accordance with the preferred embodiment of the invention.

The system is initially powered up at block 700. It then determines, at decision block 702, if the system has fully powered up. If not, an indication is provided to the operator to contact the maintenance organization at block 704.

If the system does power up properly, the sleep screen display is provided to the operator at 706. The operator, at block 708, can then choose to log on to the system. At 710 a decision is made as to whether or not operator log on is complete. If it is not, an access denied display is provided at 712 and the system returns to the sleep screen mode 706.

If logon is complete, the system enters the select mode 714. Here, an operator can select from one of five different modes, namely key operator mode at block 716, semi-automatic mode at block 718, automatic mode at block 720, machine setup mode at block 722 or shutdown logout mode at block 724.

If the operator selects key operator mode 716, the system determines whether or not the operator has inserted into the console a maintenance key and turned the key to the operator position at 730. If the key has not been properly inserted, an access denied mode is entered at 732. If, however the proper maintenance key has been inserted, a mode 734 is entered which determines whether or not the operator has the required access level as indicated by, for example, the operator entering an appropriate password at 734. If the operator is determined to not have the required access level, the access denied mode 732 is entered.

However, if the operator does have the required access level, he is then given the option of entering a calibration mode 740 or a supervisory mode 742. If the operator enters the calibration mode, he is then able to perform a force mode test 743 to calibrate the system load cell, and a linear mode 744 to calibrate the encoder to determine that the encoder reading corresponds to the actual linear displacement of the actuator.

If the operator enters the supervisory mode at 742, the system then tests as to whether or not the operator has the required access level at 745, such as by having the operator enter a predetermined password. If it is determined that the operator does not have the required access, the system enters the access denied mode at 746. However if the operator does have the required access level, the system enters the operator profile mode 748, wherein the operator is allowed to enter specific loading files, such as of the type set forth in FIG. 2, for cable to be tested.

Out of the maintenance key position 730, the operator given an option of entering the manual mode 750. The manual mode 750 allows an operator to directly enter, via a keypad, data relating to the cable under test, such as the cable part number.

The operator then enters the input parameters at block 752. Upon entering the input parameters at 752, the system responds by moving the actuator to the load position at 754. In the load position the operator then loads the cable at its fixed end at block 56. Once the cable is loaded at the fixed end position, the operator then closes the safety cover at block 758. Then, the operator loads the free end of the cable into its home position at block 760. The operator then closes a safety cover over the home position at block 762 and initiates the proof load cycle at 764. If all covers have not been closed, as determined by proximity switches at the covers, a test fails at 766. An open cover indicator is given to the operator at 768 and the operator proceeds to close the covers at block 758 or 762.

If, at cover closed test 766, the covers are indicated as being closed, a test is made to determine whether or not the home fixture has been "homed" at 770. That is, has the system been calibrated by bringing the home position fixture, which attaches to the free end of the cable, opposite the home position sensor to accurately calibrate the system? If the system has not been properly "homed", a home access indicator 770 is given to the operator at 772. This causes the operator to move to the machine setup mode 722. Out of the machine setup mode 722, the operator proceeds to assure alignment to the home axis position at 774. This then sequences back to the select mode 714 for the operator to choose the appropriate mode of the operation.

If, out of the "axis homed" test 770 it is determined that the system has been properly homed, the proof load testing is applied to the cable at block 780. Thus, at block 780 the cable is given a predetermined load versus time testing, an example of which is set forth in FIG. 2.

After the test has been completed, at block 782 the system processes the results and prints them for use by the operator. In addition, at block 784 a test is made to determine whether or not the resultant length of the cable is within tolerances stored for cables of that type. If the resultant length is outside of the specified tolerance, an audible alarm sounds at 786 and the operator takes appropriate action at 788, such as indicating that the cable has failed. Out of block 788 the operator can then enter a new part number at decision block 790, or can continue to process cables of the same part number at block 760.

If, at block 790, the operator decides to enter a new part number, the system enters a process dictated by the current operating mode. Thus, if the system is currently in the key operator mode 716, the system returns to operator input parameters 752. If the system is currently in the semi-automatic mode 718, the system returns to operator selects parameters mode 794, and, if the system is currently in the automatic mode 720, the system returns to operator scans in part no. mode 753.

If the operator, out of select mode 714, selects the semiautomatic mode 718, the operator is then given various choices of proof loading parameters. The operator, at block 794, selects those appropriate proof load parameters for the cable under test, and the system enters block 754 to move the actuator to the load position and repeat the cycle described above.

If the operator, out of select mode 714, selects the automatic mode 720, the operator can then, by use of a hand-held bar-code scanner, scan in the part number for the cable under test at block 753. The system then identifies this part number and recalls from memory the precise proof loading profile for the cable under test. The system then enters block 754 to move the actuator to the load position and begin the testing process as described above.

In summary, a method and apparatus for applying a predetermined proof loading to a cable and then determining the resultant cable length has been described in detail. While a preferred embodiment of the invention has been described in detail, various additions and modifications thereto maybe made by one of ordinary skill in the art, all of which fall within the true spirit and scope of the invention.

We claim:

1. Apparatus for applying a predetermined proof load to a cable under test and measuring the resultant cable length comprising:

means for fixing one end of the cable at a predetermined position;

means for attaching the free end of the cable to an actuator controlled fixture;

means for positioning said actuator controlled fixture at a home position, which home position is a predetermined distance, $L_1$, from said fixed position;

load sensor means for sensing the loading on the cable;

controller means for:
a) controllably actuating said actuator to apply a predetermined loading to said cable;
b) determining a distance, $L_2$, of said actuator controlled fixture from said home position; and
c) summing said distances $L_1$ and $L_2$ to thereby calculate the resultant cable length L.

2. The apparatus of claim 1 wherein said controller means further comprises:

means for identifying the particular cable under test;

memory means for storing the resultant cable length tolerances for the particular cable under test; and comparator means for comparing said actual resultant cable length L with said stored resultant cable length tolerances and producing an indication of said cable under test being within or outside of said tolerances.

3. The apparatus of claim 2 wherein said means for identifying the particular cable under test includes keypad means for permitting an operator of said apparatus to manually key in the part number of the cable under test.

4. The apparatus of claim 2 wherein said cable under test includes a bar-code indicating the part number for said cable, and wherein the means for identifying the cable under test includes a bar-code reader for reading said bar-code.

5. The apparatus of claim 2 wherein said controller means further includes:

means responsive to identifying the particular cable under test to indicate to an apparatus operator a specific fixed end position to which the cable under test should be affixed to thereby perform the proof loading test on the particular cable under test.

6. The apparatus of claim 3 wherein said controller means further includes:

means responsive to identifying the particular cable under test to indicate to an apparatus operator a specific fixed end position to which the cable under test should be affixed to thereby perform the proof loading test on the particular cable under test.

7. The apparatus of claim 4 wherein said controller means further includes:

means responsive to identifying the particular cable under test to indicate to an apparatus operator a specific fixed end position to which the cable under test should be affixed to thereby perform the proof loading test on the particular cable under test.

8. A method for applying a predetermined proof load to a cable under test and measuring the resultant cable length comprising the steps of:

a) fixing one end of the cable at a predetermined position;

b) attaching the free end of the cable to an actuator controlled fixture;

c) positioning said actuator controlled fixture at a home position, which home position is a predetermined distance, $L_1$, from said fixed position;

d) sensing the loading on the cable;

e) controllably actuating said actuator to apply a predetermined loading to said cable;

f) determining a distance $L_2$, of said actuator controlled fixture from said home position; and g) summing said distances $L_1$ and $L_2$ to calculate the resultant cable length L.

9. The method of claim 8 including the further steps of:

identifying the particular cable under test;

storing the resultant cable length tolerances for the particular cable under test; and comparing said actual resultant cable length L with said stored resultant cable length tolerances and producing an indication of said cable under test being within or outside of said tolerances.

10. The method of claim 9 wherein said step of identifying the particular cable under test includes the further step of:

providing keypad means for permitting an operator to manually key in the part number of the cable under test.

11. The method of claim 9 including the further steps of:

bar-coding the cable under test to indicate the part number thereof; and wherein the step of identifying the cable under test includes the step of providing a bar-code reader for reading said bar-code.

12. The method of claim 9 wherein the step of identifying the particular cable under test further includes an step of indicating to a operator the specific fixed end position to which the cable under test should be affixed to thereby perform the proof loading test on the particular cable under test.

13. The method of claim 10 wherein the step of identifying the particular cable under test further includes an step of indicating to a operator the specific fixed end position to which the cable under test should be affixed to thereby perform the proof loading test on the particular cable under test.

14. The method of claim 11 including wherein the step of identifying the particular cable under test further includes the step of indicating to an operator a specific fixed end position to which the cable under test should be affixed to thereby perform the proof loading test on the particular cable under test.

* * * * *

UNITED STATES PATENT AND TRADEMARK OFFICE
CERTIFICATE OF CORRECTION

PATENT NO.    : 6,142,023
DATED         : November 7, 2000
INVENTOR(S)   : Cole et al.

It is certified that error appears in the above-identified patent and that said Letters Patent is hereby corrected as shown below:

<u>Title page,</u>
Item [*], delete "449 and insert -- 499 --.

Signed and Sealed this

First Day of July, 2003

JAMES E. ROGAN
*Director of the United States Patent and Trademark Office*